(12) United States Patent
Pacheco et al.

(10) Patent No.: US 8,642,258 B2
(45) Date of Patent: Feb. 4, 2014

(54) IMMUNOGENICAL COMPLEX FORMED BY VACCINAL ANTIGENS ENCAPSULATED BY NANOSTRUCTURED MESOPOROUS SILICA

(75) Inventors: Ogari Pacheco, Itapira (BR); Osvaldo Augusto Sant'Anna, São Paulo (BR); Lucildes Mercure, São Paulo (BR); Jivaldo Matos, São Paulo (BR); Márcia Fantini, São Paulo (BR)

(73) Assignees: Cristalia Produtos Quimicos Farmaceuticos Ltda., Itapira (BR); Fundacao de Amparo a Pesquisa do Estado de Sao Paulo-Fapesp, Sao Paulo (BR)

( * ) Notice: Subject to any disclaimer, the term of this patent is extended or adjusted under 35 U.S.C. 154(b) by 496 days.

(21) Appl. No.: 12/066,489

(22) PCT Filed: Sep. 12, 2006

(86) PCT No.: PCT/BR2006/000182
§ 371 (c)(1),
(2), (4) Date: Jul. 21, 2008

(87) PCT Pub. No.: WO2007/030901
PCT Pub. Date: Mar. 22, 2007

(65) Prior Publication Data
US 2008/0286371 A1    Nov. 20, 2008

(30) Foreign Application Priority Data

Sep. 12, 2005 (BR) .......................... 0503817

(51) Int. Cl.
C12Q 1/70 (2006.01)
A61K 39/00 (2006.01)
A61K 39/295 (2006.01)
A61K 39/116 (2006.01)

(52) U.S. Cl.
USPC ...... 435/5; 424/184.1; 424/201.1; 424/202.1; 424/203.1; 977/906

(58) Field of Classification Search
None
See application file for complete search history.

(56) References Cited

U.S. PATENT DOCUMENTS

| 5,057,296 | A | 10/1991 | Beck | |
|---|---|---|---|---|
| 5,102,643 | A | 4/1992 | Kresge et al. | |
| 2002/0051794 | A1 | 5/2002 | Soni et al. | |
| 2004/0005352 | A1* | 1/2004 | Lopez et al. | 424/450 |
| 2004/0101822 | A1* | 5/2004 | Wiesner et al. | 435/5 |
| 2006/0018966 | A1* | 1/2006 | Lin et al. | 424/484 |

FOREIGN PATENT DOCUMENTS

| WO | WO-01/12221 | 2/2001 |
|---|---|---|
| WO | WO-2005/009602 | 2/2005 |
| WO | PCT/BR2006/000182 | 9/2006 |

OTHER PUBLICATIONS

Pei et al. Effect of drying on the mesoporous structure of sol-gel derived silica with PPO-PEO-PPO template block copolymer, Journal of Colloid and Interface Science, vol. 284, pp. 222-227.*
Mercuri et al., Ordered Mesoporous Silica SBA-15: A New Effective Adjuvant to Induce Antibody Response, 2006 [Epub Dec. 13, 2005], Small, vol. 2, No. 2, pp. 254-256.*
Katiyar et al., Protein adsorption on the mesoporous molecular sieve silicate SBA-15: effects of pH and pore size, 2005, Journal of Chromatography A, vol. 1069, pp. 119-126.*
Allison, et al, J Exper Med, (1966), v. 124, p. 142-161.
Cabrera, et al, Genetics, (1982), p. 583,592.
Edelman, et al, Intern Rev Immunol, (1990), p. 51-66.
Gennari, et al, Ann Inst Pasteur/Immunol, (1987), v. 138, p. 359-370.
Hadjipetrou, et al, Scand J Immunol, (1984), v. 19, p. 219-225.
Kampschmidt, et al, J Leukocyte Biol, (1986), v. 39, p. 123-132.
Lotzova, et al, J Immunol, (1974), v. 113(3), p. 798-803.
Lotzova, et al, Biomedicine, (1975), v. 22, p. 387-392.
Matos, et al, Chem Mater, (2001), v. 13, p. 1726-1731.
Huo, et al, Science, (1995), v. 268, p. 1324(4).
Vogel, et al, Infect Immun, (1982), v. 38(2), p. 681-685.
Biozzi, et al, Curr Topics Microbio Immun, (1979), v. 85, p. 31-82.
Mercuri, L. P., et al., "Thermogravimetric Analysis of the Surface Area and Pore Volume of Mesostructured Silica SBA-15," III CBRATEC, III Congresso Basileiro de Análise Térmica e Calorimetria (2002); Original and English Abstract.
Mercuri, L. P., et al., "The adjuvant effect of SBA-15 with encapsulated Int1β and antibody production in different mice lineages," XXVI Congresso Latinoamericano de Quimica (2004); Original and English translation.
da Silva, L.C.C., et al., "DSC and XRD Estimation of Pore Diameter and Pore Wall Thickness of SBA-15 Silica," Nanoporous Materials IV, International Symposium (2005) English Abstract.

* cited by examiner

*Primary Examiner* — Benjamin P Blumel
(74) *Attorney, Agent, or Firm* — Birch, Stewart, Kolasch & Birch, LLP (57) ABSTRACT

The present invention relates to a product named "immunogenical complex", which comprises an adjuvant characterized by solid particles of highly ordinated nanostructured mesoporous silica, preferably, SBA-15 Silica, and vaccinal antigens of several natures, encapsulated in the referred to adjuvants. The immunogenical complex of the present invention allows the presentation of the antigens that compose it to lymphocytes, in a safe, gradual and extended way, which leads to a more efficient immunological memory, increases the immunogenicity of the antigen and improves the production of antibodies. This ensures an efficient immunological protection with fewer amounts of antigens and/or less repetitions of vaccinal doses. In addition, the characteristics of the immunogenical complex of the present invention promotes effective immunity induction, homogeneous in "god and bad respondent" individuals.

12 Claims, 5 Drawing Sheets

IMMUNOGENICAL COMPLEX FORMED BY VACCINAL ANTIGENS ENCAPSULATED BY NANOSTRUCTURED MESOPOROUS SILICA

The present invention relates to the immunology field.

The present invention relates to a product designated "immunogenic complex", effective in increasing immunogenicity, constituted by vaccinal antigens encapsulated by solid particles of highly ordered nanostructured mesoporous silica acting as adjuvant, as shown in the present invention. The encapsulation by mesoporous silicas protects the antigens from degradation by macrophages and extends its exposure to lymphocytes, promoting improved immune response effective for induction of antibody production, either in high or in low responder individuals. The immunogenic complex of the present invention may bring benefit for the general immunological activity to antigens of distinct types: biologically active peptides, toxins, viral and bacterial vaccines.

The immune response of human beings to vaccinal antigens varies due to particular factors. Several individuals vaccinated with the same antigen, under the same conditions, produce responses that vary in intensity and duration. Such variation is a determinant factor of the intensity and duration of vaccines protective effect.

After standardized antigenic stimulation, the individuals that reply producing protective titers of antibodies are named high responders and those that do not produce protective titers are the low or even non-responders.

The development of safe and effective strategies for improvement of the immune response, either from high or from low responders is of utmost interest. In the first case, through production of protective responses with lower amount of antigen, or long-lasting response without re-exposure to the antigen. In the second case, through production a protective response with stimuli that, otherwise, would be insufficient.

Currently, this problem is only partially solved by the use of adjuvants that are defined as materials that extend the specific immune response of the organism to certain antigen [Edelman, R.; Tacket, C. O.; *Adjuvants Intern. Ver. Immunol,* 7 (1990) 51], modifying the form through which the epitopes (antigenic determinants) are presented to cells of the immune system or raising the immunogenicity thereof. Other characteristics desirable for an adjuvant are: to sustain the stimulus period, increase the presentation time of the antigen and delay the catabolism thereof.

Apparently, many adjuvants exercise their activity by toxic actions against the macrophages. There are also adjuvants that modulate the immune response to certain antigen as, for example, inducing the predominant expression of an immunoglobulin isotype, for example an IgG. [Hadjipetrou-Kourounakis, L.; Möller, E.; *Scand. J. Immunol.,* 19 (1984) 219].

The adjuvants licensed and largely used in human vaccines are the derivatives of aluminum salts, such as aluminum hydroxide or phosphate. However, these do not induce an immunological response substantially high and long lasting or qualitatively selective in relation to the desirable subclass of IgG antibodies and to the cytokines involved.

There are other adjuvants used in veterinary such as the Incomplete Freund Adjuvant [IFA] and the Complete Freund Adjuvant [CFA] that promote the undesirable formation of nodules, abscess or granulomes in the local of administration. Other adjuvants are: Lipid A, Microspheres and Liposomes, none of which are destined for use in humans.

Thus, the interest in the development of safe and effective strategies for improvement of the immune response remains evident, either from high or low responders. In this way, the advancement in the sciences of materials area is enabling the preparation of new compounds with improved properties and potential application in several areas.

The inorganic porous solids present important industrial applications in catalytic and separation processes. These materials, due to the structural and surface properties thereof, allow the access of molecules to its nanostructures, thus increasing the catalytic and sorption activity thereof.

The porous materials currently used may be classified in three classes based on its peculiar microstructure: paracrystalline amorphous supports, materials with modified layers and crystalline molecular sieves. The differences in micro and mesostructure of these materials are important, either for its sortive and catalytic behavior, as well as in the properties used for their characterization, such as: superficial area, pores size and distribution thereof, the presence or absence of X-ray diffraction standards (XRD) and the details in such standards, and the aspect of the materials when its microstructure is studied by transmission electronic microscopy (TEM) and electrons diffraction methods.

Amorphous and paracrystalline materials represent an important class of porous inorganic solids that have been used for many years in industrial applications. Typical examples of these materials are the amorphous silica, regularly used in formulation of catalysts, and the transitive paracrystalline alumina, used as supports for acid solid catalysts and petroleum modified catalysts. The term amorphous is used in this context for indicating a material that does not present a long-range order, although nearly all materials are ordered at a certain extent, at least in local scale. An alternative term that is being used to describe these materials is: "Indifferent X-Ray". The microstructure of silica consists of particles of 10-25 nm of dense amorphous silica, with porosity resulting from empty spaces between particles. Since there is no long-range order in these materials, the pore size tends to be distributed within a wide range. This lack of order is also manifested in the X-ray diffraction standard (XRD), which usually appears without the characteristic peaks.

Paracrystalline materials, such as transitive alumina, have been presenting a wide distribution of the pores size, but well defined from the X-ray diffraction standard, that usually consists of some wide bands. The microstructure of these materials consists of small crystalline regions of condensed alumina phases and the porosity of the materials is the result of irregular empty spaces between these regions. Considering that in the case of one material or another, there is no long-range order controlling the pores size in the material, the variability in such sizes is typically very high. The pore size in these materials comprises a band named mesopores that ranges between 1.3 to 20 nm.

In contrast with these solids, structurally little defined, are the materials, which distribution of pore sizes is very narrow, since it is controlled from the crystalline nature of the materials, accurately repeated, designated as microstructures. These materials are designated as "molecular sieves", and the most important examples are the zeolytes.

Such molecular sieves, natural or synthetic, include a wide variety of crystalline silicates containing positive ions.

In general, porous substances are divided by the pore size, for example, substances with pores size of less than 2 nm are classified as microporous, between 2 to 50 nm as mesoporous substances and over 50 nm are classified as macroporous substances.

A series of mesoporous molecular sieves, including MCM-41 and MCM-48, were described in U.S. Pat. Nos. 5,057,296 and 5,102,643. These molecular sieves show a structure in which the mesopores, uniform in size, are regularly arranged.

MCM-41 has a uniform structure showing a hexagonal arrangement of direct mesopores, such as honeycomb, and has a specific surface area of 1000 m$^2$/g obtained by BET method.

Molecular sieves have been produced using inorganic or organic cations as mold. These mesoporous molecular sieves are synthesized through a liquid crystal mechanism using surfactants as molds and have the advantage that the size of the pores may be adjusted in the range of 1.6 to 10 nm, through the control of surfactant type or synthetic conditions employed during the production process.

Molecular sieves designated SBA-1, SBA-2 and SBA-3 were described in *Science* (1995) 268:1324. Its channels are regularly arranged, while the constituent atoms show an arrangement similar to that of amorphous silica. Mesoporous molecular sieves have regularly organized channels, larger than those existing in zeolytes, in this way capacitating its application in adsorption, isolation or reactions of catalytic conversion of relatively large molecules.

U.S. Pat. No. 6,592,764 found a family of high quality mesoporous silicas, hydrothermal stability and of ultra-extensive pores size, through the synthesis with the use of an amphiphilic block copolymer in acid medium. A member of the family, SBA-15, has highly ordered mesostructure, hexagonal in two dimensions (p6 mm) similar to a honeycomb. Other structures as cubic in cage form, or three-dimensional hexagonal are also formed. A calcination procedure at 500° C. yields porous structures with high BET surface area of 690 to 1040 m$^2$/g, and pores volume above 2.5 cm$^3$/g, large interplanary distances d(100) of 7.45 to 45 nm, pores size of 4.6 to 50 nm and the thickness of silica wall of 3.1 to 6.4 nm. SBA-15 may be prepared with an extensive band of pores size and thickness of pore wall at low temperature (35 to 80° C.), using a variety commercially available of biodegradable and non-toxic amphiphilic block copolymer, including tri-block polyoxyalkaline.

The unique properties of SBA-15 make it an attractive material for several applications, including bio-application, for example, fixing of biologically active species. However, no document reporting the influence of these materials on immune responsiveness was identified, on the contrary, the literature would suggest its non-exploration for this purpose.

Experiments concerning the influence of amorphous silica in the immune response, specifically on macrophages, were already carried out, however, at that time they did not involve the role of silica as adjuvant [Allison, A. C.; Harington, J. S.; Birbeck, M.; *J. Exp. Med.*, 124 (1966) 141; Kampschmidt, R. F.; Worthington, M. L.; Mesecher, M. I.; *J. Leukocyte Biol.*, 39 (1986) 123; Lotzova, E.; Cudkowicz, G.; *J. Immunol.*, 113 (1974) 798; Lotzova, E; Gallagher, M. T.; Trentin, J. J. *Biomedicine*, 22(5) 387 1975; Vogel, S. N.; English, K. E.; O'brien, A. D.; *Infect. Immun.*, 38 (1982) 681].

In another experiment [Gennari, M.; Bolthillier, Y.; Ibanez, O. M.; Ferreira, V. C. A.; Mevel, J. C.; Reis, M. A.; Piatti, R. M.; Ribeiro, O. G.; Biozzi, G.; *Ann. Inst. Pasteur Immunol.*, 138 (1987) 359.], the genetically modified mice according to the low or high antibody production were used, and in which the suspensions of colloidal silica were administered during 4 consecutive days, prior to immunization with particulated antigen, namely, heterologous erythrocytes. These studies showed that there is a significant increase in the production of antibodies of low responder animals, and this improvement would be directly related with the silica action on macrophages, affecting some of its functions, changing the viability of these cells and leading the reduction of the antigen catabolism, thus favoring the presentation of the antigen to lymphocytes.

Thus, these effects were analyzed comparing the responses of mouse strains that express distinct characteristics in relation to the functionality of its macrophages. It was achieved using an experimental model that selects the mice strains with the phenotypes of maximum or minimum response of antibodies. Such strains were obtained after crossbreeding between individuals with extreme phenotypes during consecutive generations. After about 15 generations, animals presenting extreme phenotypes for the level of antibodies achieved homozygosis of the relevant alleles controlling responsiveness against certain antigen. With this model it was possible to obtain the high [H] or low [L] antibody responder lines of Selection IVA [Cabrera, W. H.; Ibanez, O. M.; Oliveira, S. L.; Sant'Anna, O. A.; Siqueira, M.; Mouton, D.; Biozzi, G.; *Immunogenetics*, 16 (1982) 583]. The differences of responses in these animals are related to the higher ($L_{IVA}$ mice line) or lower ($H_{IVA}$ mice line) macrophages catabolic activity, prejudicing or favoring, respectively, the effective presentation of antigens.

The above-mentioned studies showed that when $L_{IVA}$ mice are previously and extensively treated with amorphous silica suspensions, and then immunized with an antigen, had its antibodies production increased, approaching to the responses of the $H_{IVA}$ mice. On the other hand, [Biozzi, G.; Mouton, D.; Sant'Anna, O. A.; Passos, H. C.; Gennari, M.; Reis, M. H.; Ferreira, V. C. A.; Heumann, A. M.; Bouthillier, Y.; Ibanez, O. M.; Stiffel, C.; Siqueira, M.; *Current Topics In Microbiology Immunology*, 85 (1979) 31.], in another similar experimental model, in which $H_{III}$ and $L_{III}$ mice obtained by an independent genetic selection III were used, the modulation of antibody production of the low responder mice was not observed, after treatment with the same suspension of amorphous silica. It must be stressed that in these $H_{III}$ and $L_{III}$ animals, the high or low levels of antibodies production, does not correlate with the functionality of its macrophages, but to the potentiality of its lymphocytes.

These studies were fundamental to give support to understand the in vivo role of macrophages in immunization processes, in addition to showing that for an efficient adjuvant used in the induction of immunity it should protect the antigen administered against the highly catabolic activity of macrophages and suitably present the antigenic determinants to lymphocytes.

In large vaccine campaigns, uniform immunization products and processes are generally adopted for a large and heterogeneous group of individuals. Under these conditions, the production of variable titers of antibodies can be observed, some non-protective. It hinders the efficient immunization of part of the individuals.

Such fact is explained by the mechanisms shown in the above-mentioned experiments and originates from the phenotype variability of the individuals of the same specie, which may be interpreted by the efficient form or not of presentation of the epitope to the lymphocytes.

For example, individuals with lymphocytes effector activity that could be classified from normal to very high, or macrophages activity from reduced to normal, have a tendency to react more promptly, in relation to the production of antibodies, since the probability of the antigen to be identified more efficiently by the lymphocytes is great. These would be the "high responder" individuals in a natural population.

On the contrary, individuals that present from normal to reduced lymphocytes activity, and very high macrophages activity have a tendency to more rapid catabolize the antigen administered. It leads to a lower exposure of the antigen to lymphocytes and to an ineffective immune response. These would be the "low responder" individuals in a natural population. This situation favors a natural selection of more resistant pathogens.

It is necessary to develop more efficient vaccines that would favor and promote the production of protective antibody titers, even in individuals that are low responders to the current vaccine formulations. Therefore, it is important that this differentiated cellular behavior must be taken into consideration in the selection of the adjuvant, seeking to minimize the influence of the differentiating factors.

The application of this concept does not exist yet, and we miss products and/or vaccines produced in accordance thereof.

One objective of the present invention is to show that antigens incorporated or encapsulated in nanostructured mesoporous silica form a highly effective immunogenic complex that is efficient in the induction of an immune response and that such nanostructured mesoporous silicas do not affect the viability and phagocytic capacity of macrophages in culture.

The present invention relates to a new immunogenic complex constituted by antigens of several natures, encapsulated by highly ordered nanostructured mesoporous silicas that act as adjuvants, improving the induction of immunity and the production of antibodies to antigens, distinct concerning its nature, structure and complexity.

The immunogenic complex according to the present invention relates to the product resulting from the combination of an antigen and particles of nanostructured mesoporous silicas in specific proportions.

The immunogenic complex of the present invention allows the effective immunization of the individuals that are low responders to products and processes currently used. It originates from more safe and effective presentation of the antigen to the lymphocytes.

The immunogenic complex of the present invention is constituted by at least one antigen, which is incorporated or encapsulated by the particles of nanostructured mesoporous silicas. In addition to effectively acting as immunization adjuvant, silica particles also serve as support or matrix for bioactive species, in this case, immunogens.

The antigens that may be used in the formation of the immunogenic complex of the present invention include biologically active peptides, toxins, and viral and bacterial vaccines.

Although a wide range of nanostructured mesoporous silica may be used as adjuvants in the preparation of the immunogenic complex of the present invention, preferably, the silica designated as SBA-15 is used.

The highly ordered nanostructured mesoporous silica, SBA-15, is composed of silicon oxide particles with regular cavities and uniform in size between 2 to 50 nanometers. The antigen is set in these nanocavities for the encapsulation thereof. At the same time, this protects the degradation by macrophages and carries it to gradual and more efficient presentation to the lymphocytes, increasing the efficacy of the immune process.

Methods of preparation of SBA-15 silica and similar mesoporous materials are described in scientific articles (Zhao et al., *Science* (1998) 279:548; *J. Am. Chem. Soc*. (1998) 120:6024; Matos et al., *Chem. Mater*. (2001) 13:1726), and in U.S. Pat. No. 6,592,764.

The objective of the present invention is also to present an incorporation or encapsulation process of the antigen in nanostructured mesoporous silica, for preparation of the immunogenic complex.

The encapsulation of the antigens on silica occurs, in general, by means of a process that comprises a mixture of a solution previously prepared containing the antigen with a silica suspension, both diluted in physiological solution with pH of 7.4. The weight proportion of the antigen in relation to silica may range from 1:5 to 1:50, preferably is 1:25. This preferred proportion might be read as 1 μg of antigen to 25 μg of silica. The preparations are preferably carried out at room temperature and maintained under occasional stirring until about two hours prior to inoculation time.

Another objective of the present invention is to present the use of immunogenic complex in preparation of vaccine compositions for prophylactic use.

Pharmaceutical compositions, containing the immunogenic complex of the present invention and a pharmaceutically acceptable carrier, diluent or excipient, are appropriate for medical and veterinary use.

One advantage of the present invention consists in the use of the immunogenic complex to promote the induction of identical immune response in both high and low responder individuals with fewer amounts of antigens. This aspect has a relevant economic and social importance to public health.

The antigen is the raw material with higher cost for production of vaccines. The reduction of the necessary amount for induction of efficient immune response may lead to a substantial reduction in production cost of many vaccines.

On the other hand, the production of larger amounts of doses with the same antigen amount has implications that surpass its simple economic aspects. There are antigens which production speed is limited even in the absence of economic limiting factors. During epidemics, the optimization and maximization of the immunization potential of smaller quantities of antigens may be essential for saving millions of lives.

Another very important aspect of the present invention consists in the extension of the stimuli period, through the increase of the time for presentation of the antigen. It results in the induction of more efficient immunological memory, guaranteeing protection with lower number of doses. Several vaccines need the administration of 3 or more doses and periodic reinforcement to induce efficient protection. The sustained presentation of the antigen may cause the reduction in the number of revaccinations in some cases.

This possibility is of great impact in public health since there is a low adhesion of many parents to regular vaccination programs, vaccinating their children mainly during large campaigns published by the media. The possibility of inducing protective immunity with lower number of doses would minimize the lack of adhesion problem, taking more advantage of the campaigns and efficiently immunizing millions of children, without need for returning.

DESCRIPTION OF FIGURES

FIG. 1. Small angle X-Ray diffraction of SBA-15 silica (NC) (natural calcined) and SBA-15 (GC) (ground calcined).

FIG. 2. Isotherm of nitrogen adsorption at 77K and the corresponding pore size distribution (PSD) of calcined silica SBA-15.

FIG. 3. Images of Transmission Electron Microscopy (TEM) of calcined silica SBA-15.

FIG. 4. Determination of mouse antibodies of the IgG isotype anti-Intimin 1β of *Escherichia coli*, when comparing the adjuvant property of SBA-15 with other adjuvants after administration by the oral, intraperitoneal and subcutaneous routes.

The following examples are described as an illustration and there is no intention to use it for limiting the scope of the present invention.

EXAMPLE 1

Preparation and Characterization of Silica SBA-15

Component of the Immunogenical Complex as Immunization Adjuvant

In a reactor, 4 g of tri-block copolymer Pluronic P123 was dispersed, with magnetic stirring at 40° C., in 28 g of deionized water and 122 g of 2 M HCl solution. Then, 8.6 g of TEOS are added for obtaining a homogeneous solution under mechanical and magnetic stirring at 40° C. About 15 minutes, after the addition of TEOS, the formation of the jelly-like precipitate may be observed. The gel is maintained under stirring at 40° C. for 24 hours and, then, transferred to a Teflon-lined autoclave and placed in a sterilizer at a controlled temperature of 100° C. for 2 days. Then the solid product is filtered off, washed with deionized water and air dried at room temperature. Finally, the synthesized sample is calcined under dry $N_2$ flow at a flow rate of 100 mL.min$^{-1}$ at 540° C., using a heating rate of 1° C.min$^{-1}$. After heating for 5 hours at 540° C., the flow of nitrogen gas is changed to air, without interruption of the process, and calcination continue for 3 hours more.

The ordered bidimensional structure of SBA-15, in the form of channels in hexagonal symmetry, was evaluated by small angle X-Ray diffraction (SAXRD) and measures of $N_2$ adsorption (to define the structural and surface properties, in relation to the content of polymer present in the preparation of the material) and by transmission electronic microscopy (TEM). The results of the material characterization are resumed in Table 1 and illustrated by FIGS. 1, 2 and 3 of the present invention. Such characteristics are appropriate for considering the material as an excellent matrix for several molecular hosts.

TABLE 1

| Results of SBA-15 characterization | |
|---|---|
| Parameter | Result |
| Small angle X-Ray diffraction (SAXRD) | 12.7 nm (127 Å) |
| Specific surface area (a) | 900 m$^2$/g |
| Total pore volume | 1.39 cm$^3$/g |
| Maximum pore size (w)* | 11.6 nm (116 Å) |
| Thickness of silica wall (b)** | 1.1 nm (11 Å) |

*Obtained by the pore size distribution (PSD);
**b = a − w

Figure 1:
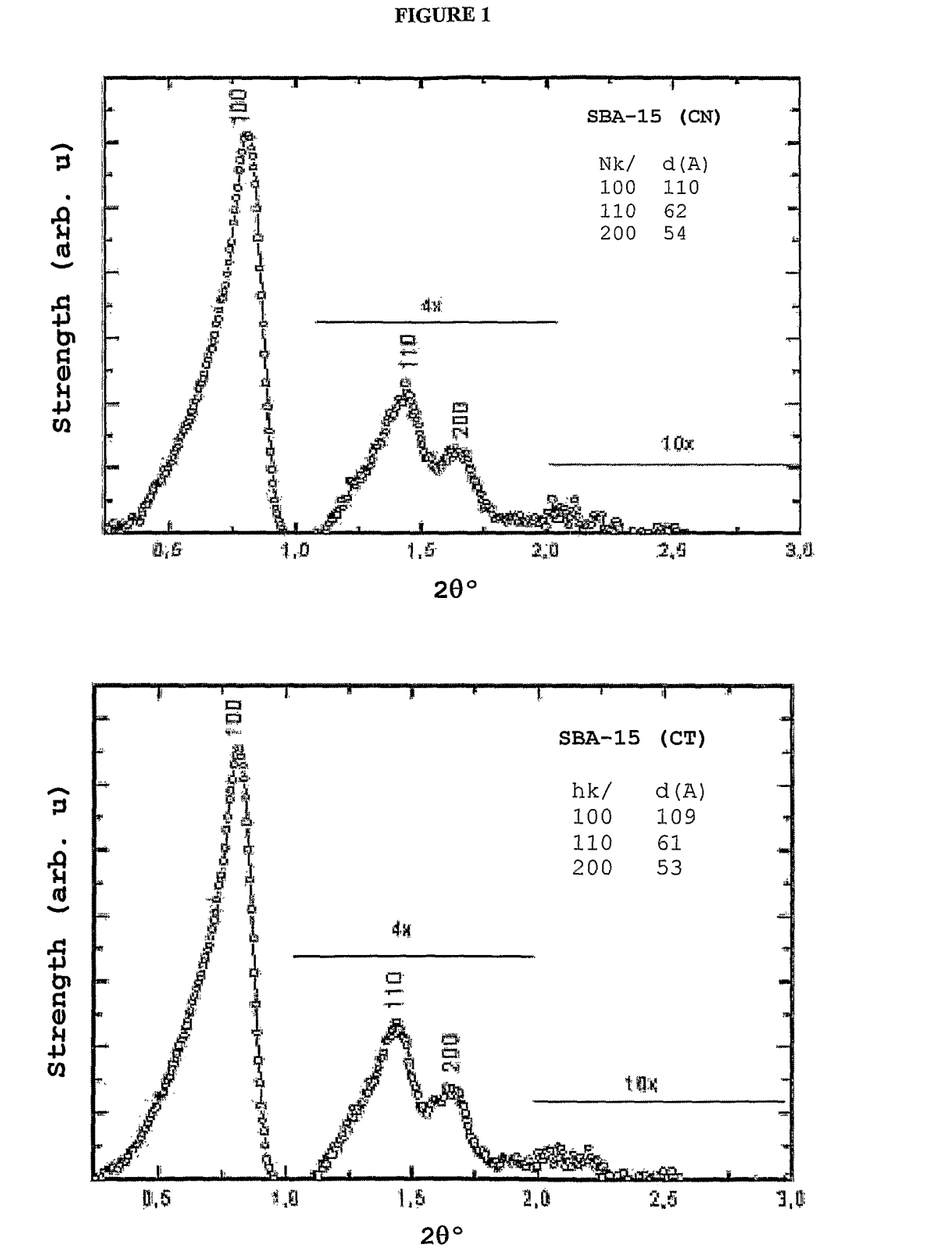

FIG. 1 shows the results of small angle X-Ray diffraction (SAXRD) obtained for the SBA-15 sample of calcined hexagonal type, in natural state (NC) and ground (GC). The results evidence that the structure of the ordered mesoporous materials (diffraction peaks) does not change after grinding the powders in agate mortar. The analysis and indexation of peaks are made after removal of the non-structured spreading background.

Figure 2:
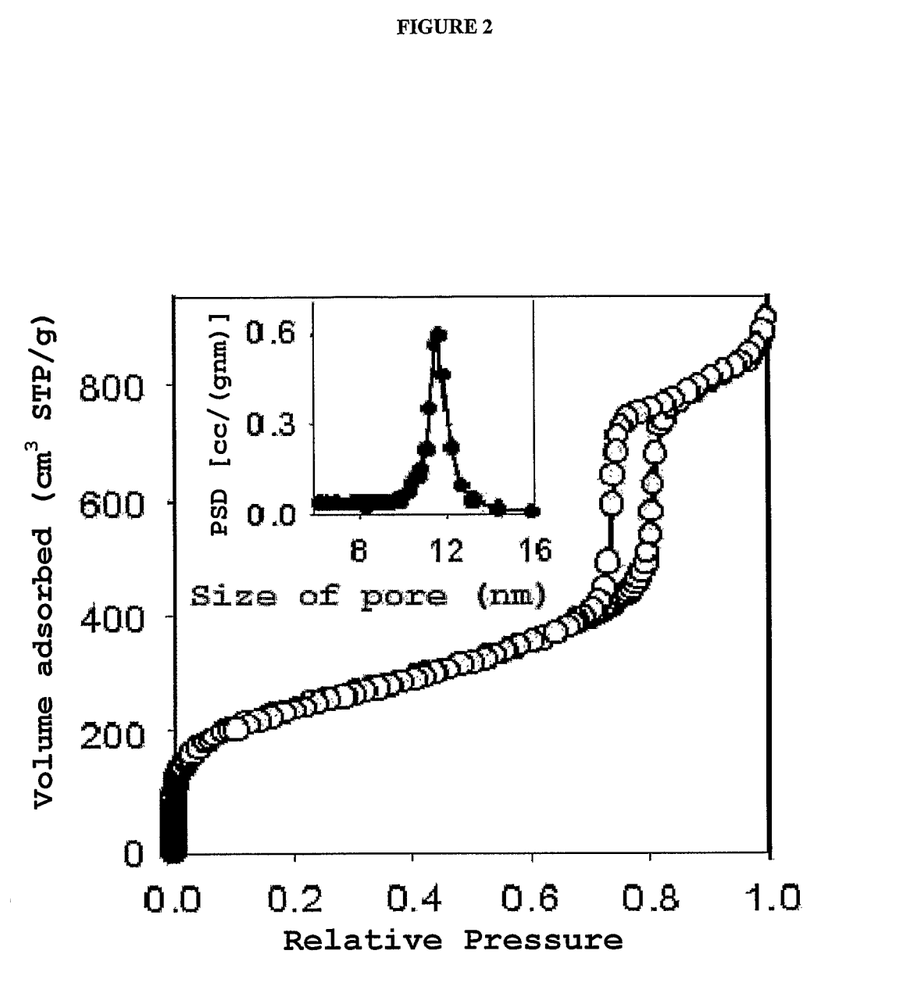

FIG. 2 shows the isotherm of nitrogen adsorption for calcined silica SBA-15, which presented a high degree of ordination, as can be deduced from the declivity in isotherm adsorption in the step of capillary condensation.

Figure 3:
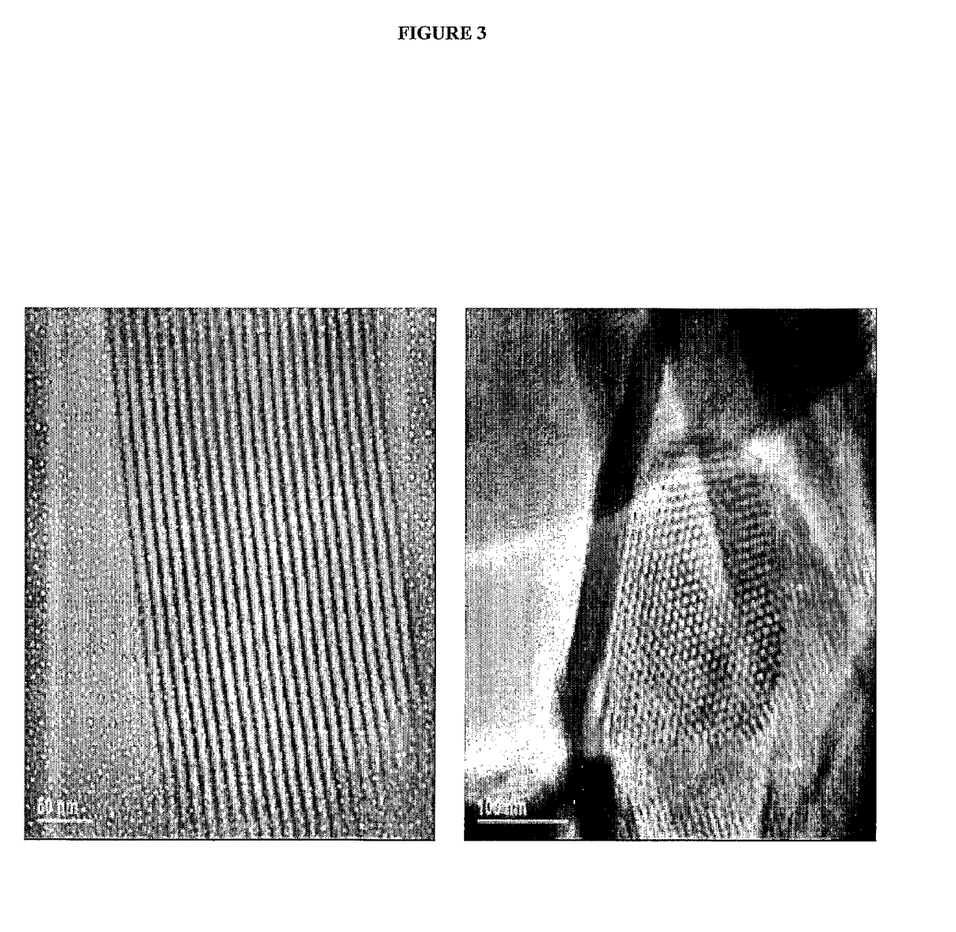

FIG. 3 shows the transmission electron microscopy (TEM), which was used to characterize the structural order of calcined silica SBA-15, where the order of parallel channels, particular of such type of material, can be observed.

EXAMPLE 2

Determination of the Adsorption Percentage of the Model Antigen by SBA-15

Using bovine serum albumin [BSA] as antigen, mixtures were made with SBA-15 at different proportions and, then, determination of adsorption percentage of antigen by silica for each proportion was made. According to the results presented in Table 2, the proportion of 1 μg of BSA to 25 μg of SBA-15 showed high adsorption percentage of BSA by SBA-15.

TABLE 2

| Determination of the best proportion for adsorption of Bovine Serum Albumin [66 kDa] in Silica SBA-15. | |
|---|---|
| BSA:SBA-15 | Adsorption % |
| 1:5 | 27.5 |
| 1:10 | 65.5 |
| 1:25 | 91 |

However, it is important to mention that due to the diversity of antigens that can compose the immunogenic complex of the present invention, the optimization of the proportion between the antigen and SBA-15 should be reconsidered in function of the complexity of the antigen.

EXAMPLE 3

Demonstration of SBA-15 Effects on Macrophages

Experiments in vitro showed that nanostructured silica SBA-15 does not affect the viability neither interferes in the macrophages phagocytic capacity originating from the medulla, maintained in culture for up to 30 hours. To the contrary, indicates to potentialize the phagocytosis through these cells. Table 3 shows that the treatment or not with SBA-15 does not substantially interfere in the phagocytosis process of yeast cells in Strains: genetically selected for a low response [$L_{IVA}$], genetically heterogeneous [SWISS], or isogenic [BALB/c].

TABLE 3

| In vitro experiment with macrophages of different mice strains | | |
|---|---|---|
| STRAIN | INFECTED Presence of yeasts | No. OF YEASTS |
| $L_{IVA}$ | | |
| 20 μg SBA-15 + yeast 2 h | 68.2% | 496 |
| 20 μg SBA-15 + yeast 17 h | 61.8% | 350 |
| 10 μg SBA-15 + yeast 2 h | 78.9% | 474 |
| 10 μg SBA-15 + yeast 17 h | 65.2% | 326 |
| 2.5 μg SBA-15 + yeast 2 h | 79.5% | 503 |
| 2.5 μg SBA-15 + yeast 17 h | 67.8% | 379 |
| Yeast 2 h | 53.9% | 217 |
| Yeast 6 h | 59.2% | 230 |
| Yeast 17 h | 82.8% | 472 |
| Yeast 21 h | 59.9% | 224 |
| Yeast 30 h | 50.2% | 164 |
| SWISS | | |
| 20 μg SBA-15 + yeast 2 h | 84.9% | 591 |
| 10 μg SBA-15 + yeast 2 h | 81.7% | 528 |

TABLE 3-continued

In vitro experiment with macrophages of different mice strains

| STRAIN | INFECTED Presence of yeasts | No. OF YEASTS |
|---|---|---|
| 10 µg SBA-15 + yeast 17 h | 70.8% | 325 |
| 2.5 µg SBA-15 + yeast 2 h | 81.9% | 468 |
| 2.5 µg SBA-15 + yeast 17 h | 74.7% | 448 |
| Yeast 2 h | 78.2% | 479 |
| Yeast 6 h | 73.3% | 437 |
| Yeast 17 h | 54.1% | 284 |
| Yeast 21 h | 56.2% | 218 |
| Yeast 30 h | 53.9% | 195 |
| BALB/c | | |
| Yeast 2 h | 82% | 622 |
| Yeast 6 h | 76.8% | 438 |
| Yeast 21 h | 68.5% | 424 |
| Yeast 30 h | 51.5% | 209 |

EXAMPLE 4

Adjuvant Effect of the Immunogenic Complex (Antigen:SBA-15) on Anti-Intβ Antibodies and Anti-Poison *Micrurus ibiboca* when Compared with the Adjuvants Regularly Used in Mice Strains Groups of 4-5 mice genetically selected according to high production of antibodies [$H_{III}$ line], or to the low response [$L_{IVA}$ line], and mice of isogenic line [genetically identical animals] BALB/c were tested in distinct experiments. The potential effect of SBA-15 was evaluated with the measurement and the comparison of response to the recombinant protein β-intimine [Int1β] of 16.5 kDa of the bacteria *Escherichia coli*, adsorbed in SBA-15 [1:10 Int1β:SBA-15] or admixed to Incomplete Freund Adjuvant (IFA). The response to antibodies formation was also evaluated for the total venom of the Elapidae snake family, *Micrurus ibiboboca* genus, composed by at least 20 proteins with molecular weight ranging from 84 to 7 kDa, adsorbed in SBA-15 [1:10 Micru:SBA-15], comparing the response to this venom admixed in IFA. All these experiments were carried out following immunizations by subcutaneous route. Data presented in Tables 4 and 5 [mean±standard deviation ($\log_2$)] confirm that SBA-15 is as efficient as IFA, promoting high antibody titers and being efficient in the immunological memory induction.

TABLE 4

Anti-Int1β Titer [$\log_2$] 15 days after immunization

| | SBA-15 | | IFA | |
|---|---|---|---|---|
| Mice strain | N | x ± σ | n | x ± σ |
| $L_{IVA}$ | 4 | 11.3 ± 0.5 | 4 | 4.5 ± 0.5 |
| $H_{III}$ | 4 | 11.3 ± 0.4 | 3 | 13.3 ± 0.5 |
| BALB/c | 4 | 6.2 ± 3.2 | 5 | 9.8 ± 2.3 |

TABLE 5

Anti-Micrurus Titer [$\log_2$] 14 days after immunization

| | SBA-15 | | IFA | |
|---|---|---|---|---|
| Mice strain | n | x ± σ | n | x ± σ |
| $L_{IVA}$ | 4 | 8.1 ± 0.5 | 3 | 5.2 ± 0.3 |
| BALB/c | 4 | 9.2 ± 1.3 | 4 | 6.4 ± 0.8 |

In addition, SBA-15, contrary to what occurs upon administration of IFA, does not lead to the formation of an apparent granuloma and, the local inflammatory response is insipid and, when measured at 24-48 hours after the inoculation of the immunogen in SBA-15 by subcutaneous route presents very reduced levels of monocytes and nuclear polymorphous.

There is no apparent change in the behavior and vitality of mice that received SBA-15 relatively to the control animals and, followed for 11 months, no morphological change is observed in treated animals.

EXAMPLE 5

Figure 4:
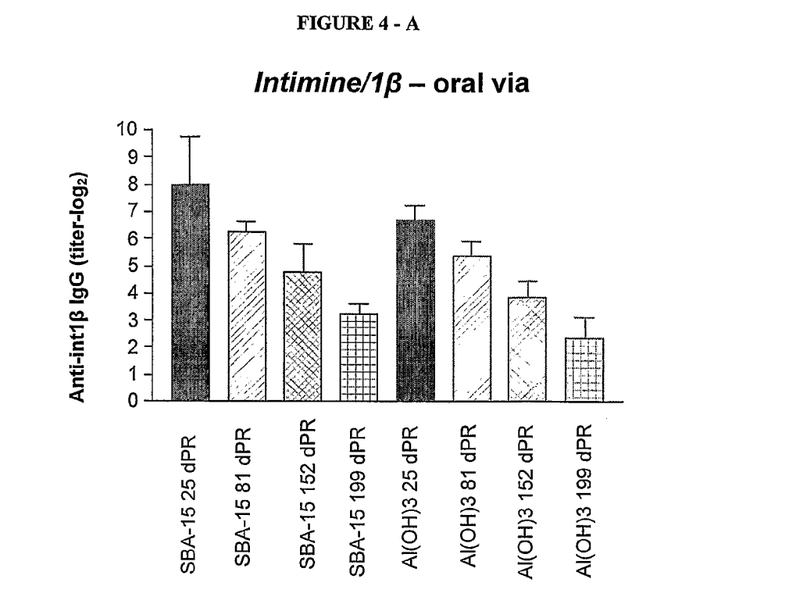

The Adjuvant Effect of the Immunogenic Complex (Antigen:SBA-15) on Anti-Intβ Antibodies in Function of Time when Compared with the Adjuvants Normally Used In another series of assays, groups of BALB/c mice were immunized with Int1β (from *Escherichia coli*) in SBA-15, Al(OH)$_3$ by oral route, or Int1β in SBA-15, Al(OH)$_3$ and IFA by subcutaneous and intraperitoneal route. The anti-Int1β responses were followed during a long time. FIG. 4 presents the responses to the protein Intimin 1β of *Escherichia coli* according to distinct immunization routes. Means and standard deviations of isogenic Strain BALB/c mice, followed up to 199 days [d] during the primary responses [PR], immunized with the known adjuvants Al(OH)$_3$, Incomplete Freund Adjuvant (IFA) and the original SBA-15 nanostructured silica. It can be noted that the antibody levels remained high during throughout the analyzed period, especially in the group that received the antigen in SBA-15.

Altogether the results clearly show that SBA-15 is a non-immunogenic, non-toxic and efficient carrier promoting both high response to antibodies and efficient immunological memory.

Highly ordered nanostructured mesoporous silicas, illustrated in the present invention by SBA-15 silica, provide promising systems for vaccinal preparations or compositions.

The invention claimed is:

1. An immunogenic complex consisting essentially of i) particles of ordered nanostructured mesoporous silica, having pores of 2 to 50 nm in diameter, and ii) at least one antigen, wherein the proportion of antigen to silica particles is 1:5 to 1:50 and the antigen is encapsulated by the particles of mesoporous silica, which act as an adjuvant for immunization.

2. The immunogenic complex according to claim 1, wherein the at least one antigen is selected from the group consisting of proteins, biologically active peptides, toxins, viruses and bacteria.

3. The immunogenic complex according to claim 2, wherein the antigen is a bacterial protein antigen or a viral protein antigen.

4. The immunogenic complex according to claim 1, wherein the ordered nanostructured mesoporous silica is a SBA-15 mesoporous silica.

5. The immunogenic complex according to claim 1, wherein the proportion of antigen to silica particles is 1:25.

6. The immunogenic complex of claim 1, that provides prolonged presentation of antigen to lymphocytes and results in improved immunologic memory response.

7. A vaccine comprising the immunogenic complex of claim 1, and a pharmaceutically acceptable carrier, diluent or excipient.

8. A method for producing an immunogenic complex comprising mixing particles of ordered nanostructured mesoporous silica, having pores of 2 to 50 nm in diameter, with at least one antigen, wherein the antigen and silica particles are mixed in a ratio of 1:5 to 1:50, whereby the antigen is enbapsulated by the particles of mesoporous silica, which act as an adjuvant for immunization.

9. The method according to claim 8, wherein the at least one antigen is selected from the group consisting of proteins, biologically active peptides, toxins, viruses and bacteria.

10. The method according to claim 9, wherein the antigen is a bacterial protein antigen or viral protein antigen.

11. The method according to claim 8, wherein the highly ordered nanostructured mesoporous silica is a SBA-15 mesoporous silica.

12. The immunogenic complex according to claim 1, in which the pores of the mesoporous silica are hexagonally close packed.

* * * * *